United States Patent [19]

Dummer et al.

[11] Patent Number: 4,746,759
[45] Date of Patent: May 24, 1988

[54] PROCESS FOR THERMAL CRACKING OF 1,2-DICHLOROETHANE TO FORM VINYL CHLORIDE

[75] Inventors: Gerhard Dummer, Burgkirchen; Klaus Haselwarter, Emmerting; Hermann Klaus, Marktl; Ludwig Schmidhammer, Haiming; Rudolf Strasser, Burghausen, all of Fed. Rep. of Germany

[73] Assignee: Wacker-Chemie GmbH, Fed. Rep. of Germany

[21] Appl. No.: 923,327

[22] Filed: Oct. 27, 1986

[30] Foreign Application Priority Data

Dec. 6, 1985 [DE] Fed. Rep. of Germany ....... 3543222

[51] Int. Cl.$^4$ .................... C07C 17/24; C07C 17/34
[52] U.S. Cl. ................................................. 570/226
[58] Field of Search ............................... 570/226, 227

[56] References Cited

U.S. PATENT DOCUMENTS

| 2,724,006 | 11/1955 | Krekeler | 570/226 |
|---|---|---|---|
| 3,476,955 | 11/1969 | Krekeler et al. | 570/238 |
| 3,903,182 | 9/1975 | Rechmeier et al. | 570/226 |
| 3,998,706 | 12/1976 | Fruhwirt et al. | 570/262 |
| 4,590,318 | 5/1986 | Longhini | 570/226 |
| 4,665,243 | 5/1987 | Burts, Jr. | 570/226 |

FOREIGN PATENT DOCUMENTS 770917  3/1957  United Kingdom ............... 570/227

Primary Examiner—J. E. Evans
Attorney, Agent, or Firm—Bierman & Muserlian

[57] ABSTRACT

An improved process for the preparation of vinyl chloride from 1,2-dichloroethane (EDC) wherein 0.10 to 0.15 % by weight of carbon tetrachloride based on EDC, is used as a cracking promoter and the CHCl$_3$ content is limited to less than 200 ppm. Before being fed to the cracking zone, the EDC is brought almost to the boiling point at 15 to 31 bar and then expanded to 10 to 16 bar with flashing EDC vapors and the fraction which has remained liquid is vaporized externally, and the combined EDC gas streams are heated, after being fed into the cracking furnaces, so that the energy required for cracking is already supplied in the first 75 to 85% of the reaction zone, whereby a conversion of 60 to 70% is obtained at residence time from 10 to 25 seconds and the exit temperature from the reaction zone is 485° to 510° C.

2 Claims, 1 Drawing Sheet

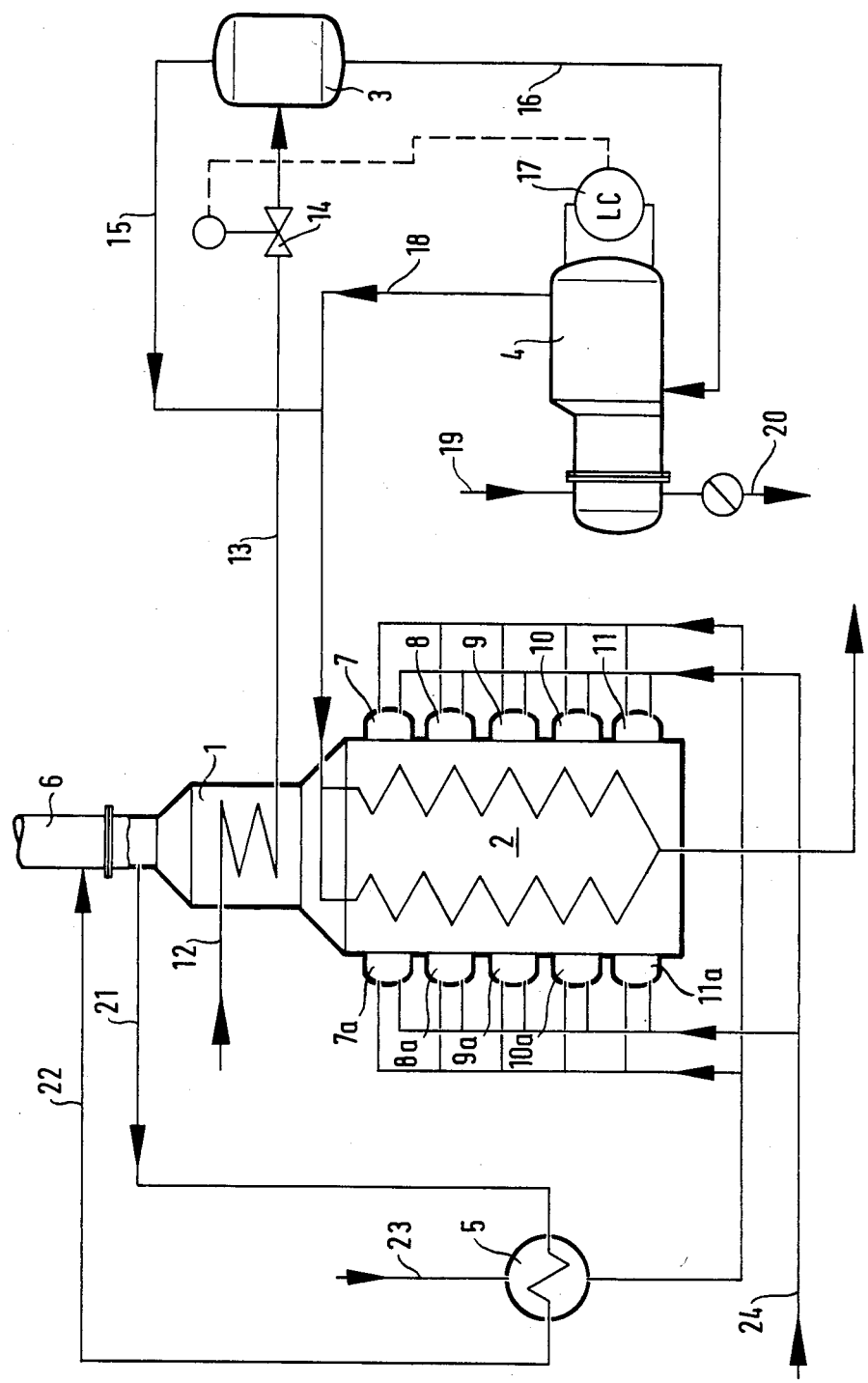

PROCESS FOR THERMAL CRACKING OF 1,2-DICHLOROETHANE TO FORM VINYL CHLORIDE

STATE OF THE ART

It is known to produce vinyl chloride monomer on a large industrial scale by incomplete thermal cracking of purified EDC wherein EDC in vapor form is heated indirectly in a pyrolysis furnace and is cracked at temperatures of 400° C. to 600° C. at a pressure of 15 to 36 bar absolute to give VCM and hydrogen chloride, the conversions being kept through appropriate temperature control in the cracking furnace at only 50 to at most 60%, based on the total throughput of EDC vapor [compare Schulze et al, Chem. Industrie, Vol. XXXVI, (August 1984) page 469]. Accordingly, substantial amounts of unconverted EDC must be recycled to the cracking reaction, it first being necessary to carry out careful purification of the unconverted EDC by separating off the vinylacetylene, 1,3-butadiene, chloroprene, 1-chloro-1,3-butadiene and numerous other chlorohydrocarbon by-products formed as well as aromatics because these by-products in part exert an inhibiting action and in part also promote the deposition of carbon and tar.

For example, at degrees of conversion of only 50 to at most 60%, based on total throughout of EDC, 1.06 to 1.6 metric tons (t) of unconverted EDC per ton of VCM produced must, in addition to the specific EDC amount of about 1.6 t of EDC per t of VCM required for the production of VCM at the time, be purified by distillation and vaporization in the cracking furnace. This means that the resulting average specific energy consumption is that required for processing (handling) a total of 2.66 to 3.2 t of EDC per t of VCM produced.

OBJECTS OF THE INVENTION

It is an object of the invention to drastically reduce the specific amount of unconverted EDC involved per t of VCM produced to values of between 0.68 and 1.05 t of EDC/t of VCM produced by going over to deep cracking, i.e. by adjusting the EDC conversion to 60 to 70%, based on the total EDC throughput, and thereby, in combination with other measures, to substantially reduce the specific consumption of utilities for the process steps of "purifying unconverted EDC" and "vaporizing purified EDC in the cracking furnace", without having to accept lower quality of the VCM produced or reductions in selectivity of the total process or reduced furnace life (capacity losses), though VCM production is greatly increased.

This and other objects and advantages of the invention will become obvious from the following detailed description.

THE INVENTION

The improved process of the invention for the preparation of vinyl chloride by thermal cracking of 1,2-dichloroethane obtained in liquid form in the purification by distillation at a temperature from 125° C. to 155° C. under corresponding pressures and vaporization, without intermediate storage, in an external vaporizer with addition of carbon tetrachloride as a cracking promoter, at temperatures from 400° to 600° C. under a pressure from 10 to 16 bar absolute and with conversions from 50 to 60% at residence times from 0.1 to 30 seconds in the reaction zone and with partial utilization of the heat content of the flue gases from the cracking furnace firing for preheating liquid 1,2-dichloroethane to almost the boiling point at the corresponding pressure before it enters the external vaporizer, and with the use of air preheated to about 100° C. for the cracking furnace firing, the improvement comprises (a) maintaining the carbon tetrachloride content in the liquid 1,2-dichloroethane between 0.10 and 0.15% by weight, based on 1,2-dichloroethane, and at the same time adjusting the chloroform content in the liquid 1,2-dichloroethane to below 200 mg/kg of 1,2-dichloroethane;

(b) preheating the liquid 1,2-dichloroethane, which is at 125° to 155° C. and contains carbon tetrachloride according to (a) in the convection section of the cracking furnace at a liquid pressure of 15 to 31 bar absolute almost to the boiling point, with utilization of a major part of the heat content of the flue gases from the cracking furnace firing, and expanding the preheated liquid 1,2-dichloroethane to a pressure from 10 to 16 bar absolute after it has left the convection section of the cracking furnace, about 18 to 70% by weight of the total 1,2-dichloroethane being vaporized;

(c) separating the 1,2-dichloroethane obtained as vapor in Step (b) from the liquid fraction, then vaporizing this liquid fraction in an external vaporizer at a pressure of 10 to 16 bar absolute and feeding the combined streams of dichloroethane vapor, which also contain the carbon tetrachloride in the form of vapor, to the reaction zone of the cracking furnace at such rates that the hourly loading is 1,100 to 1,500 t of 1,2-dichloroethane per $m^2$ of cracking tube cross-section; and (d) setting 1,2-dichloroethane conversions from 60 to 70% at a mean residence time from 10 to at most 15 seconds, based on the fired part of the reaction zone, by firing the cracking furnace so that the temperature level is 425° to 455° C. even in the region of the transition from the shock section to the radiant section of the reaction space, the temperatures are 460° to 480° C. approximately in the middle of the reaction zone and the remainder of total energy required is already supplied at about 75 to 85% of the total tube length of the reaction zone comprising the shock section and the radiant section, to maintain exit temperatures from 485° to 510° C. at the coil end.

The invention results in an improved and more economical process for the preparation of vinyl chloride (VCM=vinyl chloride monomer) by so-called deep cracking of 1,2-dichloroethane (EDC=ethylene dichloride) at moderate temperatures at the coil end of the reaction zone. At the same time, the heat content of the flue gases of the cracking furnace firing is utilized economically to produce EDC flash vapor and to superheat the combustion air required for the cracking furnace firing, and it is thereby possible, while reducing the consumption of utilities for EDC vaporization in the cracking furnace and for treating the unconverted EDC, and while reducing the specific fuel consumption for the cracking furnace firing, to increase the capacity of an existing cracking furnace, without major investments, to about 150% of the original design specification, without an increase in the formation of by-product and coke and without a deterioration in the quality of the VCM produced. Furthermore, this invention makes a not insignificant contribution to general protection of the environment, because the flue gas temperature from the cracking furnace firing is substantially lowered by the invention.

In a special, preferred embodiment of the process, the heat content of the flue gases from the cracking furnace firing which leave the convection section of the cracking furnace at a temperature from 240° to 540° C. is utilized for superheating the combustion air, which is at about 100 degrees, for the cracking furnace firing to temperatures from 200° to 500° C. with simultaneous cooling of the flue gases to temperatures from 140° to 180° C.

The total amount of EDC to be purified and vaporized is then, according to the invention, only 2.28 to 2.65 t of EDC/t of VCM produced, i.e. they are thus reduced by about 14 to 28% based on a conventional procedure with EDC conversions of 50 to at most 60%. In combination with the generation of EDC flash vapor by the invention, this results in a mean saving of about 0.35 t of the steam, used in general for heating such processes, per t of VCM produced.

For firing a cracking furnace, disregarding the energy required for the vaporization of EDC, about 3 giga-joules (GJ) of heat energy must be supplied per t of VCM to be produced, about 80% of this quantity of heat being required for preheating liquid EDC in the convection section of a cracking furnace to almost the boiling point at a pressure of 10 to 16 bar absolute, for superheating EDC vapor to the cracking temperature and for the endothermic cracking process. However, about 20% of this heat is lost with the flue gases from the cracking furnace firing since heat recovery is hardly economical due to the resulting relatively low flue gas temperature level of about 270° C. to 330° C.

As a consequence of economic necessity in present times, processes have therefore been proposed recently for recovering a part of the amount of heat required for cracking EDC—as far as this heat appears as the heat content of the cracked gases. In addition, recovery of waste heat from the flue gases from a cracking furnace firing with generation of steam is also practiced in some cases. Because of the relatively low flue gas temperature, however, such processes are not very economical. Even if the flue gas temperature is raised as taught in commonly assigned U.S. patent application Ser. No. 786,811 filed Oct. 11, 1985, and now abandoned, steam generation still requires relatively high investment costs.

It is therefore a further object of the invention to raise the flue gas temperature in the upper part of the firebox before entry into the convection section of the cracking furnace by controlled introduction of radiant energy at certain points of the reaction zone to such an extent that the liquid EDC, which is to be preheated in the convection section, is preheated at corresponding liquid pressures to a boiling temperature far above that corresponding to a pressure of 10 to 16 bar absolute, to generate EDC flash vapor by expansion to a pressure of 10 to 16 bar absolute and, by combination with the measures described in U.S. patent application Ser. No. 786,811, to maintain such a high flue gas temperature level downstream of the outlet from the convection section of the cracking furnace that the combustion air for the cracking furnace firing, which air has been preheated to about 100° C. by methods already known, can be superheated by heat exchange with the flue gases, to economize on valuable primary energy, which is not available in unlimited quantities, for example in the form of natural gas.

It is known that the conversion and thermal cracking of EDC is heavily dependent on the temperature (British Pat. No. 1,266,676) and the highest possible EDC conversion is generally desired for economic reasons. Increased conversion has, however, the consequence that by-products of cracking and coke formation also increase. The by-products which can be detected are saturated and unsaturated aliphatic hydrocarbons as well as aromatic hydrocarbons such as, for example, vinylacetylene, 1,3-butadiene, 2-chloro-1,3-butadiene, 1-chloro-1,3-butadiene, isomeric dichlorobutadienes, tetrachlorobutadiene, 1,1-dichloroethylene, 1,1-dichloroethane, methyl chloride, chloroform, ethyl chloride, carbon tetrachloride and benzene. Since the boiling points of some of these impurities and that of EDC are very close, the said by-products are gradually concentrated in the recycled unconverted EDC.

The increasing uncontrolled concentration of the substances has several adverse effects. Firstly, the cracking coil cokes more rapidly so that, in conjunction with higher reaction temperatures required for increasing the conversion, even more coke is produced. Additional coke deposited in the cracking coil causes a higher pressure drop across the reaction system and frequent coke removal from the cracking coil thus becomes necessary, which is tantamount to a reduction in plant capacity. In addition, both high reaction temperatures which are necessary for increasing the conversion and increased coke deposition in the cracking coil automatically lead to higher wall temperatures of the cracking tube material because, on the one hand, with the raising of the reaction temperature due to the endothermic cracking process, the wall temperature must be raised correspondingly to set a sufficiently large temperature difference for the required specific heat flux, and because, on the other hand, due to the heat-insulating properties of coke, the required temperature difference between the product stream and the tube wall must correspondingly be even higher in the event of relatively heavy coke deposition. However, higher wall temperatures cause material damage such as high-temperature corrosion by HCL, carburization by the precipitation of carbides and, in the worst case, "metal dusting", as a result of which the cracking tubes can split open so that fires and explosions can occur. In addition, the impurities in VCM generally also increase with a rise in cracking by-products. Separation of 1,3-butadiene, vinylacetylene and methyl chloride from VCM by distillation can, however, be accomplished only with a very expensive distillation arrangement.

U.S. Pat. No. 2,755,315 discloses that the cracking reaction can be accelerated by the addition of carbon tetrachloride as a cracking initiator which manifests itself either by an increase in EDC conversion at a comparable reaction temperature or by the possibility of lowering the reaction temperature at a comparable EDC conversion. In the said U.S. patent, 0.5% based on EDC feed is given as the lower limit for the catalytic activity of carbon tetrachloride, but the presence of such large quantities of carbon tetrachloride in the cracking reaction also favors the formation of undesired by-products such as, for example, chloroform and methyl chloride. Because of its boiling point, methyl chloride predominantly appears in the VCM, and it can be separated from VCM only at great technical expense. In spite of the preceding purification by distillation, chloroform passes via the unconverted, recycled EDC back into the cracking process because, together with other lowboiling components present in crude EDC, it can be separated off by distillation only under more severe conditions, and in the cracking process causes extremely extensive formation of coke with all its deleterious secondary phenomena, a coke of particularly coarse-grained structure being formed which sometimes has very poor adhesion properties and is thus blown together with the product stream out of the cracking tube and then leads to increased coke depositions and erosions in the downstream product quench.

In U.S. Pat. No. 3,222,407, 0.05 to 5% of chlorine together with 100 to 2,500 ppm of carbon tetrachloride are used as a reaction accelerator, but at the high temperatures of the cracking reaction, chlorine causes extensive corrosion of the cracking tube material.

According to DE-B No. 2,349,838, the thermal cracking of EDC is carried out in the presence of 0.01 to 0.3% by weight of carbon tetrachloride Ebased on EDC but it has been found that the accelerating effect of carbon tetrachloride at concentrations of <0.1% by weight of carbon tetrachloride in EDC is very small, above all in the case of relatively short mean residence times in the heated part of the reaction zone which, in combination with the change in furnace heating, is a subject of the invention. Moreover, even at concentrations of >0.15% by weight of carbon tetrachloride in EDC, coke formation increases so dramatically that a marked rise in pressure drop across the reaction zone is detectable within only a few weeks, especially if the cracking reaction is initiated at a relatively early point as a result of the arrangement of the cracking furnace firing in accordance with the invention.

In combination with the arrangement of the cracking furnace firing in accordance with the invention or with shortened mean residence times in the fired part of the reaction zone, a concentration of 0.1 to 0.15% by weight, preferably 0.11 to 0.13% by weight of carbon tetrachloride in EDC has in the invention a particularly favorable effect with respect to increasing the EDC conversion or lowering the reaction temperature at the coil end without obtaining an increased amount of undesired by-products and coke. Rather, the addition of carbon tetrachloride within the range of the invention in combination with the changed cracking furnace firing, surprisingly accomplishes a reduction in the formation of 1,3-butadiene, vinylacetylene and methyl chloride. There are several possibilities for maintaining the carbon tetrachloride concentration of the invention in EDC while simultaneously maintaining a chloroform level of <200 ppm by weight (mg/kg) in EDC: on the one hand, the content of chloroform which is mainly formed in the ethylene oxychlorination reaction in washed crude EDC can be sharply lowered by separating the so-called secondary chloroform, which is formed by caustic cleavage of chloral hydrate dissolved in the oxychlorination aqueous effluent during the alkaline stripping of this effluent and is present in the organic stripper condensate, from the process after phase separation and passing it to another use.

As a result, it is possible, at a reduced overall chloroform content in the feed to the light-ends column in the separation of light ends and water from washed crude EDC, for example according to U.S. Pat. No. 3,998,706, to control the distillation process so that less than 200 ppm of chloroform and 1,000 to 1,500 ppm (mg/kg) of carbon tetrachloride are present in the bottom of this light-ends or azeotrope column and hence also in the purified EDC which is obtained at the top of the heavy-ends column. On the other hand, the desired EDC blend can be obtained by operating the light-ends column in accordance with U.S. Pat. No. 4,351,976. If the procedure of U.S patent application Ser. No. 779,257 filed Sept. 27, 1985 is followed, the predominant amount of the carbon tetrachloride employed as a cracking promoter is recycled together with the unconverted EDC into the cracking furnace since the boiling points of carbon tetrachloride and EDC are almost identical. Thus, only minimal amounts of carbon tetrachloride have to be made up which can be easily accomplished, for example by appropriate manipulation of the partial condensation temperature in the distillation process according to U.S. Pat. No. 3,998,706, and can best be monitored by an on-line process chromatograph in the EDC feed to the cracking furnace. Furthermore, it is of course also possible to add carbon tetrachloride in appropriate amounts to the EDC from outside and this is best done before the EDC is preheated and vaporized. However, it is also possible to add it after preheating or to feed it directly into the cracking reactor.

In combination with the accelerating action of carbon tetrachloride within the addition range of the invention, increased EDC conversions of 60 to 70%, based on EDC feed, without a significant rise in the exit temperature at the coil end of the cracking zone, are obtained by a further measure of the invention, if a major part of the total required heat energy is introduced into the reaction zone at a relatively early point and firing of the reaction zone is terminated at only about 75 to 85% of the total tube length of the reaction zone comprising the shock section and radiant section. It was surprising here that, in spite of the resulting earlier start of the cracking reaction, i.e. an overall extended residence time of formed VCM in the reaction system, no increased formation of by-products and coke is observed, particularly since it is generally known that the further reaction of formed VCM to give interfering by-products and coke is highly dependent on the partial pressure which, however, rises correspondingly with increasing EDC conversion. It was also surprising that, with an overall shortened fired reaction zone, the resulting, likewise shortened mean residence time in the reaction zone is still sufficient to achieve such high EDC conversions at moderate reaction temperatures at the coil end.

As a result of the change of the invention in the cracking furnace firing, the temperature of the flue gases rising from the shock section and radiant section naturally increases from about 600° C. in the case of conventional cracking furnace firing to about 670° to 700° C., under otherwise constant specific fuel requirement. This higher flue gas temperature level can therefore be used for generating EDC flash vapor by bringing liquid EDC, which is at 125 to 155 degrees and which is obtained, for example, in accordance with U.S. patent application Ser. No. 786,811, in the convection section of the cracking furnace by heat exchange with the flue gases from cracking furnace firing, in the liquid form at a corresponding pressure to temperatures which are far above the boiling point corresponding to a pressure of 10 to 16 bar absolute and subsequently expanding it to 10 to 16 bar absolute. This means of generating EDC flash vapor is admittedly known per se, but it is economically feasible only if the liquid EDC can be preheated to a sufficiently high temperature, and this can be accomplished by the combination, already described, of the measures of the invention without increasing the specific fuel requirement for the cracking reactor. This saves quite considerable quantities of heating steam for the external vaporization of EDC or the desired increase in output from an existing plant can thus be achieved without problems even in the case of a bottleneck in EDC vaporization.

Due to the higher preheating of the liquid EDC in the convection section of the cracking furnace, more heat would be removed from the flue gas if the liquid EDC were to enter at a temperature of about 100° C., which is necessary, as experience shows, to avoid dew point corrosion at the end of the finned tubes of the convection section. Further utilization of the heat content of the flue gases leaving the convection section would then no longer be economical in any sense because of the unduly low temperature level. If, however, the liquid EDC is introduced at a temperature from 125° to 155° C., as is possible when the distillation process described in U.S. patent application Ser. No. 786,811 is used, the temperature level of the flue gases leaving the convection section is, in spite of increased liquid EDC preheating, still so high that the heat content of these flue gases can be used for generating steam or—because it is more economical overall, involving lower investment costs—for superheating, according to the invention, combustion air at about 100 degrees for the cracking furnace firing. This leads to a saving of valuable primary energy which is not available in unlimited quantities, for example in the form of natural gas.

In the following examples there are described several preferred embodiments to illustrate the invention. However, it is to be understood that the invention is not intended to be limited to the specific embodiments. All temperatures in this specification are given as degrees Celsius (°C.) and $Nm^3$ signifies $m^3$ reduced to standard condition (0° C., 1.013 hPa).

EXAMPLE 1

Referring to the FIGURE, 71 t/h of EDC, to which inter alia 1,220 ppm weight of carbon tetrachloride and 130 ppm by weight of chloroform were added and which were obtained in the liquid form at a temperature of about 140° C. in the distillation process described in U.S. patent application Ser. No. 786,811 were pumped via line 12 into the convection section 1 of the cracking furnace and preheated by heat exchange with the flue gases which exited at a temperature of 672° C. from the shock and radiant section 2 of the cracking furnace to 243° C. at a liquid pressure of 26 bar absolute, the EDC still being just in the liquid state. The superheated liquid EDC was expanded via line 13 in the level control valve 14, controlled by the level controller 17 of the external EDC vaporizer 4, to 14 bar absolute, 28.027 kg/h of EDC passing into the vapor state. After separation of this EDC vapor in the gas/liquid separator 3 from 42,973 kg/h of EDC which still remained liquid, the residual liquid EDC passed under level control via line 16 into the external vaporizer 4 which was supplied via line 19 with 5.5 t/h of 22 bar steam (condensate discharge via line 20), where the EDC vaporized and was passed via line 18 together with the EDC flash vapor, leaving the gas/liquid separator 3 via line 15, into the shock and radiant section 2 of the cracking furnace.

The cracking furnace was arranged as a two-pass system and the internal tube diameter of the two cracking coils was 192 mm, giving a specific loading of 1,225 t of $EDC/m^2$. In the shock and radiant section 2 of the cracking furnace, the cracking tubes were fired by the four burner planes 7/7a to 10/10a so that, in the region of the transition from the shock section into the radiant section at about 30% of the total tube length of the reaction zone, the product temperature was 435° C., the product temperature of both passes in the middle of the reaction zone was 468° C. and the remaining required total energy had been supplied at about 80% of the total tube length (that is to say the burner planes 11/11a were turned off), so that a product exit temperature of 497° C. was established at the coil end of each pass and the mean residence time in the fired reaction space was 11 seconds. The cracking reached a conversion of 64%, based on EDC fed, corresponding to a VCM output of 28.5 t/h after separation of 17 t/h of HCl and 25.5 t/h of unconverted EDC, the following VCM product quality being obtained:

7.0 ppm by weight of 1,3-butadiene
6.8 ppm by weight of vinylacetylene
32 ppm by weight of methyl chloride
remainder: VCM.

The flue gases left the convection section 1 of the cracking furnace at a temperature of 360° C. and were fed via line 21 to the heat exchanger 5 in which air at 100 degrees at 23 at a rate of 34,500 kg/h preheated to 10° C., for example according to U.S. patent application Ser. No. 786,811 was superheated to 330° C. by heat exchange with the flue gases before it was mixed with 2,066 $Nm^3$/h of natural gas fed via line 24, and used in the burners of planes 7/7a to 10/10a for firing the cracking furnace. The flue gases thus cooled to 160° C. and were discharged via line 22 into the stack 6.

The operating period of the cracking furnace was 7 months, that is to say it was necessary only after 7 months' running to decoke the furnace because of a rise in the pressure drop across the cracking coils due to coking. The specific steam consumption for EDC vaporization was 0.19 t/t of VCM, and the specific natural gas consumption was 72.5 $Nm^3$/t of VCM. By comparison, in a conventionally fired cracking unit at 55% EDC conversion, the specific steam consumption for EDC vaporization was about 0.39 t/t of VCM and the specific natural gas consumption was approximately 84 $Nm^3$/t of VCM.

COMPARISON EXAMPLE A

The procedure followed was analogous to Example 1 with the exception that the carbon tetrachloride in the EDC was 2,000 ppm by weight. Under otherwise identical conditions, VCM was obtained at a slightly lower product exit temperature of 495° C. at the coil end which contained the following impurities:

10 ppm by weight of 1,3-butadiene
9.5 ppm by weight of vinylacetylene
40 ppm by weight of methyl chloride.

After only 6 weeks, the pressure difference in the cracking furnace rose due to increased coke deposition to such an extent that the throughput had to be lowered by 20% to be able to still vaporize sufficient EDC in the vaporizer 4 by the available heating steam at 22 bar pressure. After 3 months' running, the furnace had to be decoked since the output continued to fall.

COMPARISON EXAMPLE B

Analogously to Example 1, EDC with a content of 800 ppm by weight of carbon tetrachloride was cracked and to maintain a comparable EDC conversion of 64%, the firing had to be modified so that the product temperature was 515° C. at the coil end. The VCM produced had the following product quality:

15 ppm by weight of 1,3-butadiene
14.5 ppm by weight of vinylacetylene
55 ppm by weight of methyl chloride.

Due to increased coke deposition because of the higher exit temperature, the cracking furnace had to be decoked after 3.5 months' running.

COMPARISON EXAMPLE C

Analogously to Example 1, EDC with a carbon tetrachloride content of 1,220 ppm by weight was cracked, but at a chloroform content of 500 ppm by weight. Under otherwise identical conditions and with approximately the same VCM quality, more coke was formed which partially deposited in the cracking coils so that the operating period of the furnace was only 5 months, but was partially also discharged into the quench where it caused erosions which made it necessary after 2 running campaigns to repair the eroded parts of the quench by surface welding.

COMPARISON EXAMPLE D

EDC with carbon tetrachloride and chloroform contents analogous to Example 1 was cracked under conventional crackin furnace firing the total natural gas requirement being distributed over 5 burner planes (i.e. also additionally to burner planes 11/11a) so that the resulting mean residence time in the fired reaction zone was about 18 seconds. Even at 58% EDC conversion and a specific loading of 1,000 t of EDC/m$^2$ of tube cross-section, the following product temperatures and flue gas temperatures were then established:

At the transition from the shock section into the radiant section: 390° C.
in the middle of the reaction zone: about 445° C.
at the coil end: about 525° C.
flue gas at the exit from the shock section: 605° C.

Even if EDC entered the convection section of the cracking zone at 140 degrees, only 15% of EDC flash vapor could be obtained by expansion from 14 bar to 10 bar if the required combustionair was also to be superheated from 100° C. to 330° C. This gave a specific steam consumption of 0.31 t/t of VCM for EDC vaporization, a specific natural gas consumption of 74 Nm$^3$/t of VCM and a product output of only 21 t/h of VCM of the following quality:

19 ppm by weight of 1,3-butadiene
18 ppm by weight of vinylacetylene
65 ppm by weight of methyl chloride Due to extensive coke deposition in the cracking tubes, the operating period of the furnace was only 2.5 months.

Various modifications of the process of the invention may be made without departing from the spirit or scope thereof and it should be understood that the invention is intended to be limited only as defined in the appended claims.

What we claim is:

1. In a process for the preparation of vinyl chloride by thermal cracking of 1,2-dichloroethane obtained in liquid form in the purification by distillation at a temperature from 120° C. to 155° C. under corresponding pressures and vaporization, without intermediate storage, in an extenal vaporizer with addition of carbon tetrachloride as a cracking promoter, at temperatures from 400° to 600° C. under a pressure from 10 to 16 bar absolute and with conversions from 50 to 60% at residence times from 0.1 to 30 seconds in the reaction zone and with partial utilization of the heat content of the flue gases from the cracking furnace firing for preheating liquid 1,2-dichloroethane to almost the boiling point at the corresponding pressure before it enters the external vaporizer, and with the use of air preheated to about 100° C for the cracking furnace firing the improvement comprising (a) maintaining the carbon tetrachloride content in the liquid 1,2-dichloroethane between 0.10 and 0.15% by weight, based on 1,2-dichloroethane, and at the same time adjusting the chloroform content in the liquid 1,2-dichloroethane to below 200 mg/kg of 1,2-dichloroethane;

(b) preheating the liquid 1,2-dichloroethane, which is at 125° to 155° C. and contains carbon tetrachloride according to (a), in the convection section of the cracking furnace at a liquid pressure of 15 to 31 bar absolute almost to the boiling point, with utilization of a major part of the heat content of the flue gases having a temperature of 670° to 700° C. from the cracking furnace firing, and expanding the preheated liquid 1,2-dichloroethane to a pressure from 10 to 16 bar absolute after it has left the convection section of the cracking furnace, about 18 to 70% by weight of the total 1,2-dichloroethane being vaporized;

(c) separating the 1,2-dichloroethane obtained as vapor in Step b) from the liquid fraction, then vaporizing this liquid fraction in an external vaporizer at a pressure of 10 to 16 bar absolute and feeding the combined streams of dichloroethane vapor, which also contain the carbon tetrachloride in the form of vapor, to the reaction zone of the cracking furnace at such rates that the hourly loading is 1,100 to 1,500 tons of 1,2-dichloroethane per m$^2$ of cracking tube cross-section; and (d) setting 1,2-dichloroethane conversions from 60 to 70% at a mean residence time from 10 to at most 15 seconds, based on the fired part of the reaction zone, by firing the cracking furnace so that the temperature level is 425° to 455° C. even in the region of the transition from the shock section to the radiant section of the reaction space, the temperatures are 460° to 480° C. approximately in the middle of the reaction zone and the remainder of total energy required is already supplied at about 75 to 85% of the total tube length of the reaction zone comprising the shock section and the radiant section to maintain exit temperatures from 485° to 510° C. at the coil end.

2. The process of claim 1 wherein the heat content of the flue gases from the cracking furnace firing, which leave the convection section of the cracking furnace at a temperature from 240° to 540° C., is utilized for superheating the combustion air, which is at about 100 degrees, for the cracking furnace firing to temperatures from 200° to 540° C., with simultaneous cooling of the flue gases to temperatures from 140° to 180° C.

* * * * *